(12) United States Patent
Park et al.

(10) Patent No.: US 7,459,141 B2
(45) Date of Patent: Dec. 2, 2008

(54) TECHNETIUM-99M-LABELED ORGANIC GERMANIUM NANOCOLLOIDS, METHOD OF PREPARING THE SAME AND USE THEREOF

(75) Inventors: Sang Hyun Park, Daejeon (KR); Hui Jeong Gwon, Daejeon (KR); Myung Woo Byun, Daejeon (KR)

(73) Assignee: Korea Atomic Energy Research Institute, Daejon (KR)

( * ) Notice: Subject to any disclaimer, the term of this patent is extended or adjusted under 35 U.S.C. 154(b) by 179 days.

(21) Appl. No.: 11/474,717

(22) Filed: Jun. 26, 2006

(65) Prior Publication Data

US 2007/0224117 A1  Sep. 27, 2007

(30) Foreign Application Priority Data

Mar. 23, 2006  (KR) .................. 10-2006-0026508

(51) Int. Cl.
*A61K 51/00* (2006.01)
*C07J 13/00* (2006.01)
(52) U.S. Cl. .......................... 424/1.11; 534/14
(58) Field of Classification Search .................. 424/9.1, 424/1.69, 1.73, 1.11, 1.37, 1.65; 435/7.23; 534/14
See application file for complete search history.

(56) References Cited

OTHER PUBLICATIONS

Silvia, S.J.,, et al., Potential Technetium Small Molecule Radiopharmaceuticals, Chem. Rev., vol. 99, pp. 2205-2218, 1999.
Liu, Shuang, et al., 99mTc-Labeled Small Peptides as Diagnostic Radiopharmaceuticals, Chem. Rev., vol. 99, pp. 2235-2268, 1999.
Atkins, Harold L., et al., Splenic Sequestration of 99mTc Labeled . . . , Radiology, vol. 136, pp. 501-503, 1980.

*Primary Examiner*—Michael G. Hartley
*Assistant Examiner*—Jagadishwar R Samala
(74) *Attorney, Agent, or Firm*—Lucas & Mercanti, LLP

(57) ABSTRACT

Disclosed relates to organic germanium nanocolloids, to which technetium-99m ($^{99m}$Tc), a radionuclide, is labeled, method of the same, and a spleen-imaging agent including the same. According to the invention, $^{99m}$Tc-labeled organic germanium nanocolloids having high labeling efficiency and stability can be provided. Moreover, since the $^{99m}$Tc-labeled organic germanium nanocolloids of the invention are accumulated in the spleen considerably higher than the conventional spleen-imaging agent, it is possible to use the $^{99m}$Tc-labeled organic germanium nanocolloids of the present invention as a therapeutic radiopharmaceutical for the spleen imaging.

7 Claims, 4 Drawing Sheets

US 7,459,141 B2

TECHNETIUM-99M-LABELED ORGANIC GERMANIUM NANOCOLLOIDS, METHOD OF PREPARING THE SAME AND USE THEREOF

This patent application claims the benefit of priority from Korean Patent Application No. 10-2006-0026508 filed Mar. 23, 2006, the contents of which are incorporated herein by reference.

BACKGROUND OF THE INVENTION

1. Field of the Invention

The present invention relates to organic germanium nanocolloids, to which technetium-99m ($^{99m}$Tc), a radionuclide, is labeled, a method of preparing the same and a use thereof as a spleen-imaging agent.

2. Description of Related Art

In general, nuclear medicine technologies for using nuclear power in medicine definitely require the use of a radiopharmaceutical. The radiopharmaceutical is prepared by selecting an appropriate material from among various kinds of radioisotopes generated when operating a nuclear reactor and processing it for use in the diagnosis or therapy of diseases to be administered to the human body. Such a radiopharmaceutical can readily and obviously detect metastasis of cancer that is difficult or impossible to diagnose using other techniques.

When a diagnostic radiopharmaceutical is administered to the human body, it accumulates in specific internal organs of the body depending on the diagnostic purposes. Thereby, diseases occurring in various internal organs of the human body may be diagnosed. That is, when the radiopharmaceutical accumulates in the internal organs, such as the brain, bones, thyroid gland, heart, lungs, liver, spleen, kidney, etc., an image of the γ-rays emitted from the radiopharmaceutical accumulated in such internal organs can be obtained using a γ-camera. In addition to the internal organs, the radiopharmaceutical may also accumulate in cancer, inflammation, blood, etc.

Further, a therapeutic radiopharmaceutical is composed of radionuclides, which emit stronger radiation capable of killing cells despite the lower permeability of the human body and have a relatively longer half-life, compared to diagnostic radiopharmaceuticals. Such radionuclides emit α-rays or β-rays. The radionuclides emitting α-rays are highly toxic and are not readily available. Besides, it is very difficult to label such radionuclides to other materials than diagnostic radionuclides. Thus, radionuclides emitting β-rays have been used to date as radiopharmaceuticals.

Methods of preparing radiopharmaceuticals for the diagnostic and therapeutic purposes include a method of labeling a specific radioactive isotope. An exemplary radioisotope widely used at present for labeling the diagnostic radiopharmaceutical is technetium-99m ($^{99m}$Tc). Since technetium has a relatively shorter half-life of 6 hours and emits only γ-ray energy of 140 keV suitable for obtaining a γ-image, it has low toxicity to the human body and high permeability thereto. Accordingly, it is most suitable for administrating technetium to the human body to obtain a desired image, thus being widely applied to diagnostic and therapeutic radiopharmaceuticals in nuclear medicine field (Silvia, S. J., John, D, L., Potential technetium small molecule radiopharmaceuticals, Chem. Rev. 99, 2205-2218, 1999; and Shuang, L., Edwards, D. S., $^{99m}$Tc-labeled small peptides as diagnostic radiopharmaceuticals. Chem. Rev. 99, 2235-2268, 1999).

Meanwhile, the spleen is the largest lymphoid organ located under the left side of the rib cage. It is known that the spleen plays important roles in the human body such as destruction of blood cells, production of antibodies, lipoid metabolism, phagocytic function, bond marrow depression, etc. As a result of certain disease such as leukemia, lymphoma, typhoid and the like, the spleen may become very enlarged and may be ruptured easily by trauma.

Any of the technetium-labeled colloid preparations may be used for diagnosing any abnormality of the spleen. In the past, radiopharmaceuticals used for the spleen imaging include $^{99m}$Tc-sulfur colloid, $^{99m}$Tc-albumin colloid and $^{99m}$Tc-red blood cell, which have been used to demonstrate the structure of the spleen and any abnormality therein (Atkins, H. L., Goldman, A. G., Fairchild, R. G., Radiology, 136, 501, 1980).

However, the radiopharmaceuticals for the spleen imaging have had a problem that their efficiencies are decreased more or less since the amount of the radiopharmaceuticals accumulated in the spleen is very small.

Germanium is one of the non-metallic elements, which can exist in valence states of 2 and 4. It has been known that metalloid germanium has widespread applications in various fields of electronics, nuclear sciences and medicines. In general, the germanium has a low toxicity, except for the tetrahydride germanium, and there have been reported few observations on toxicity of the germanium in the human body. However, since it is known that inorganic germanium compounds are more toxic than organic germanium compounds, it is undesirable to apply the inorganic germanium compounds to the human body.

SUMMARY OF THE INVENTION

Accordingly, the inventors of the present invention, paying attention to the organic germanium compounds having widespread applications in nuclear sciences and medicines, have carried out researches aimed at a contrast agent for imaging a specific organ in the body and find that $^{99m}$Tc-labeled organic germanium nanocolloid having high labeling efficiency and stability provide an excellent effect as a contrast agent for imaging organs in the body, particularly, for imaging the spleen, thus completing the present invention.

An object of the present invention is to provide a method of preparing a $^{99m}$Tc-labeled organic germanium nanocolloid.

Another object of the present invention is to provide a $^{99m}$Tc-labeled organic germanium nanocolloid prepared via the method.

Still another object of the present invention is to provide a use of $^{99m}$Tc-labeled organic germanium nanocolloid as a spleen-imaging agent.

To accomplish the above objects, the present invention provides a method, as depicted in Scheme 1, of preparing a $^{99m}$Tc-labeled organic germanium colloid, as expressed in Chemical Formula 1, comprising the steps of:

preparing an organic germanium colloidal solution [ST 1]; and preparing a solution, in which sodium pertechnetate (Na$^{99m}$TcO$_4$) and stannous chloride (SnCl$_2$·2H$_2$O) are solved in an acidic solvent, and adding dropwise the resulting solution to the organic germanium colloidal solution to induce a reaction [ST 2].

[Scheme 1]

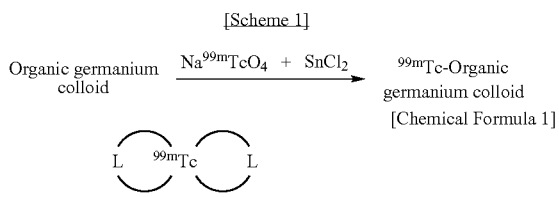

[Chemical Formula 1]

wherein L denotes an organic germanium compound.

In a method for preparing $^{99m}$Tc-labeled organic germanium nanocolloid in accordance with the present invention, the organic germanium compound expressed as L of Chemical Formula 1 includes bis-carboxyethylgermanium sesquioxide (Ge-132), spirogermanium and lactate-citrate-germanate. Among others, the bis-carboxyethylgermanium sesquioxide, expressed by Chemical Formula 2 below, may be preferably used.

[Chemical Formula 2]

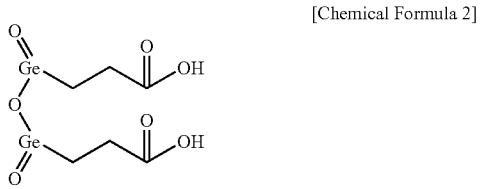

In step 1 [ST 1] of the present invention, it is desirable to maintain the pH of the organic germanium colloidal solution within a range of 3.5 to 4.5 in order to maximize the labeling efficiency of the technetium-99m. If the organic germanium colloidal solution is out of the pH range, the labeling efficiency of the technetium-99m for the organic germanium compounds deteriorates.

In step 2 [ST 2] of the present invention, the sodium pertechnetate (Na$^{99m}$TcO$_4$) is a substance used for labeling the organic germanium compound, and the labeling process is to form an organic germanium complex with a labeling objective, the organic germanium compound.

In this step, the stannous chloride (SnCl$_2$·2H$_2$O) functions as a reducing agent for reducing pertechnetate ions. Since the stannous chloride (SnCl$_2$·2H$_2$O) as a reducing agent is unstable in a basic condition, the labeling efficiency of the technetium-99m for organic germanium compounds is decreased. However, since the stannous chloride (SnCl$_2$·2H$_2$O) is relatively stable in an acidic condition, reducing power is increased, which results in the increase of the labeling efficiency. Accordingly, it is necessary to prepare the sodium pertechnetate (Na$^{99m}$TcO$_4$) and the stannous chloride (SnCl$_2$·2H$_2$O) dissolved in an acidic solvent, such as hydrochloric acid, sulphuric acid, nitric acid and the like, in step 2.

After adding dropwise the sodium pertechnetate (Na$^{99m}$TcO$_4$) and the stannous chloride (SnCl$_2$·2H$_2$O) solutions prepared as described above to the organic germanium colloidal solution prepared in step 1 [ST 1], the resulting solution is stirred for 30 minutes at room temperature, thus obtaining $^{99m}$Tc-labeled organic germanium nanocolloids.

Furthermore, the present invention provides $^{99m}$Tc-labeled organic germanium nanocolloid prepared via the above-described method.

Preferably, the present invention provides $^{99m}$Tc-labeled organic germanium nanocolloid, wherein the organic germanium compound L of Chemical Formula 1, to which technetium-99m is labeled, is one selected from the group consisting of bis-carboxyethylgermanium sesquioxide (Ge-132), spirogermanium and lactate-citrate-germanate. More desirably, the present invention provides $^{99m}$Tc-labeled Ge-132 nanocolloid, expressed by Chemical Formula 3 below, wherein the bis-carboxyethylgermanium sesquioxide (Ge-132) is used as an organic germanium compound L.

[Chemical Formula 3]

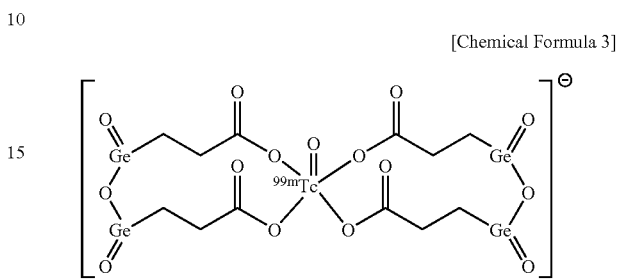

Meanwhile, since it is known that inorganic germanium compounds are more toxic than organic germanium compounds, it is undesirable to administrate the inorganic germanium compounds into the human body.

Moreover, the present invention provides a spleen-imaging agent including $^{99m}$Tc-labeled organic germanium nanocolloid expressed by Chemical Formula 1.

The organic germanium compound, to which technetium-99m is labeled, e.g., the bis-carboxyethylgermanium sesquioxide (Ge-132) of Chemical Formula 3, increases interferon activity and natural killer NK cell activity of spleen cells in a mouse 24 hours after an oral administration. Besides, it induces peritoneal macrophage activity. Its therapeutic attributes include immuno-enhancement, oxygen enrichment, free radical scavenging, analgesia and heavy metal detoxification.

After an oral administration, the bis-carboxyethylgermanium sesquioxide concentrates highly in spleen. High bis-carboxyethylgermanium sesquioxide concentrates in liver, kidney, spleen and gastrointestine tract after an intravenous (i.v) injection, specially, it concentrates in spleen and kidney.

Accordingly, the $^{99m}$Tc-labeled bis-carboxyethylgermanium sesquioxide ($^{99m}$Tc—Ge-132) nanocolloid in accordance with the present invention can be used as a contrast agent for imaging the spleen particularly, among various organs in the body.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION OF THE INVENTION

Figure 1:
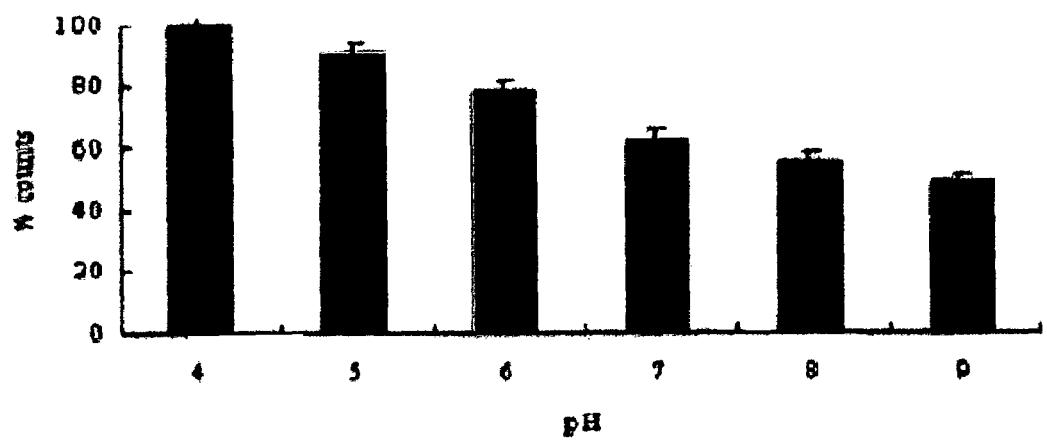
FIG. 1 is a graph showing effects of pH on labeling efficiency of $^{99m}$Tc-labeled bis-carboxyethylgermanium sesquioxide ($^{99m}$Tc—Ge-132) nanocolloids in accordance with a preferred embodiment of the present invention.

Hereinafter, a detail description of the present invention will be given with reference to the attached drawings. The present invention is not restricted to the following embodiments, and many variations are possible within the spirit and scope of the present invention. The embodiments of the present invention are provided in order to more completely explain the present invention to anyone skilled in the art.

EMBODIMENT

Preparation of $^{99m}$Tc-Labeled bis-carboxyethylgermanium sesquioxide ($^{99m}$Tc—Ge-132) Nanocolloids

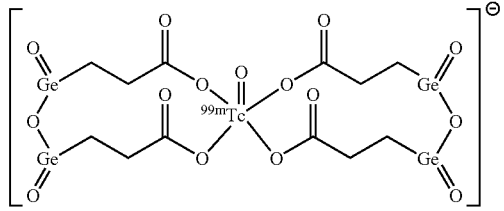

To prepare the $^{99m}$Tc-labeled bis-carboxyethylgermanium sesquioxide ($^{99m}$Tc—Ge-132), unless otherwise noted, all starting materials were obtained from commercial suppliers and used without further purification. Sodium pertechnetate (Na$^{99m}$TcO$_4$) was eluted from a $^{99}$Mo/$^{99m}$Tc generator (Unitech 500, manufactured by Samyoung Unitech Co., Ltd., Seoul, Korea) using 0.9% saline.

2 mg (4.4 µmol) of bis-carboxyethylgermanium sesquioxide (Ge-132) colloids (prepared by Geranti Pharm Inc., Seoul, Korea) were dispersed in 0.1 ml of 0.9% NaCl solution of pH 4. To this solution, 0.1 ml of Na$^{99m}$TcO$_4$ (10 mCi) and 0.1 mg of (0.44 µmol) of stannous chloride solution were added in 0.1 N HCl. Nitrogen gas was passed to degas all the solution prior to the mixing. Subsequently, the Na$^{99m}$TcO$_4$ solution and stannous chloride solution were added dropwise to the dispersed bis-carboxyethylgermanium sesquioxide (Ge-132) colloids. The resulting solution was stirred for 30 minutes at room temperature to prepare $^{99m}$Tc-labeled bis-carboxyethylgermanium sesquioxide ($^{99m}$Tc—Ge-132) nanocolloids of 99% or more.

EXPERIMENTAL EXAMPLE 1

Assessment of Labeling Efficiency of $^{99m}$Tc—Ge-132 Nanocolloids

To assess the labeling efficiency of $^{99m}$Tc—Ge-132 nanocolloids prepared in accordance with the Embodiment, an ascending instant thin layer chromatography (ITLC) using silica gel coated fiber sheets (prepared by Gelman Science Inc., Ann Arbor, Mich., USA) was carried out. Using methyl ethyl ketone MEK or physiological saline as a development solvent, $^{99m}$Tc—Ge-132 nanocolloids were developed and the results were depicted in Table 1.

TABLE 1

| Chromatographic system | | $^{99m}$Tc species at | |
|---|---|---|---|
| Support | Solvent | Origin | Solvent front |
| ITLC-SG | MEK | 100% of $^{99m}$Tc—Ge-132 | 0% of $^{99m}$TcO$_4^-$ |
| ITLC-SG | Saline | 100% of $^{99m}$Tc—Ge-132 | 0% of $^{99m}$TcO$_4^-$ |

As depicted in Table 1, free pertechnetate ($^{99m}$TcO$_4$) moving to solvent front was assessed all 0% in MEK and physiological saline, whereas, $^{99m}$Tc—Ge-132 remaining at the origin was detected all 100%. As a result, it could be understood that the labeling efficiency of technetium-99m for the bis-carboxyethylgermanium sesquioxide (Ge-132) in accordance with the present invention is very excellent.

EXPERIMENTAL EXAMPLE 2

Assessment of Stability of $^{99m}$Tc—Ge-132 Nanocolloids

To estimate the stability of $^{99m}$Tc—Ge-132 nanocolloids prepared in accordance with the Embodiment, the following experiment was executed. The $^{99m}$Tc—Ge-132 nanocolloids were stored in closed vials at room temperature and the radiolabeling efficiency was measured for 0.5, 1, 2, 3, 4, 5, 6 hours, respectively, and the results were shown in Table 2.

TABLE 2

| | Hour | | | | | | |
|---|---|---|---|---|---|---|---|
| | 0.1 | 1 | 2 | 3 | 4 | 5 | 6 |
| Labeling | 100 | 100 | 100 | 100 | 100 | 100 | 99 |

As shown in Table 2, in view of the fact that the labeling efficiency was maintained 99% up to 6 hours after labeling the $^{99m}$Tc, it was confirmed that the $^{99m}$Tc—Ge-132 nanocolloids are stable for at least 6 hours.

EXPERIMENTAL EXAMPLE 3

Effect of pH on Stability of $^{99m}$Tc—Ge-132 Nanocolloids

To identify the effects of pH on the increase and the stability of the $^{99m}$Tc—Ge-132 nanocolloids prepared in accordance with the Embodiment, the radiolabeling efficiency was measured varying pH of reaction media and the results were shown in FIG. 1.

With reference to FIG. 1, it was understood that the labeling yield (% count) according to the pH variation was decreased as the pH increased. Accordingly, it was found that it was important to control the pH of reaction media appropriately in order to enhance the labeling efficiency and the stability of the $^{99m}$Tc—Ge-132 nanocolloids.

EXPERIMENTAL EXAMPLE 4

Measurement of the Particle Size of $^{99m}$Tc—Ge-132 Nanocolloids

To measure the particle size of the $^{99m}$Tc—Ge-132 nanocolloids prepared in accordance with the Embodiment, the following analysis experiment was fulfilled using a transmission electron microscope (TEM).

The $^{99m}$Tc—Ge-132 colloidal solution was sterilized by membrane filtration (0.22 µm) and kept in sterile reaction vials for storage in a refrigerator. Then, it was spotted onto plastic-coated (carbon-stabilized) copper grids (300 mesh) and an electron micrograph of the nanocolloids was taken using a transmission electron microscope as shown in FIG. 2.

Figure 2:
FIG. 2 is a photograph of $^{99m}$Tc-labeled bis-carboxyethylgermanium sesquioxide ($^{99m}$Tc—Ge-132) nanocolloids in accordance with a preferred embodiment of the invention, taken by a transmission electron microscope (TEM)

As shown in FIG. 2, it was revealed that the $^{99m}$Tc—Ge-132 nanocolloids were all spherical and the particle size of $^{99m}$Tc—Ge-132 nanocolloids was estimated to be mostly 60 to 80 nm.

EXPERIMENTAL EXAMPLE 5

Study of Biodistribution of $^{99m}$Tc—Ge-132 Nanocolloids

Experiment for investigating biodistribution of $^{99m}$Tc—Ge-132 nanocolloids was carried out using three normal, female Sprague-Dawley rats per group. Intraperitoneal injections of 100 µCi/0.1 ml of $^{99m}$Tc—Ge-132 nanocolloids were made to the SD rats. The rats were sacrificed 5 min, 30 minutes and 60 minutes after the injections. Approximate 0.1 g of samples were taken from blood, kidney, spleen, liver, heart, lungs, stomach and intestine and weighed. Radioactivities of the samples were measured using a Beckman γ-counter and, then, the tissue concentrations were calculated to express the results as depicted as % injected dose/total tissue in FIG. 3A and as % injected dose/g tissue in FIG. 3B.

Figure 3A:
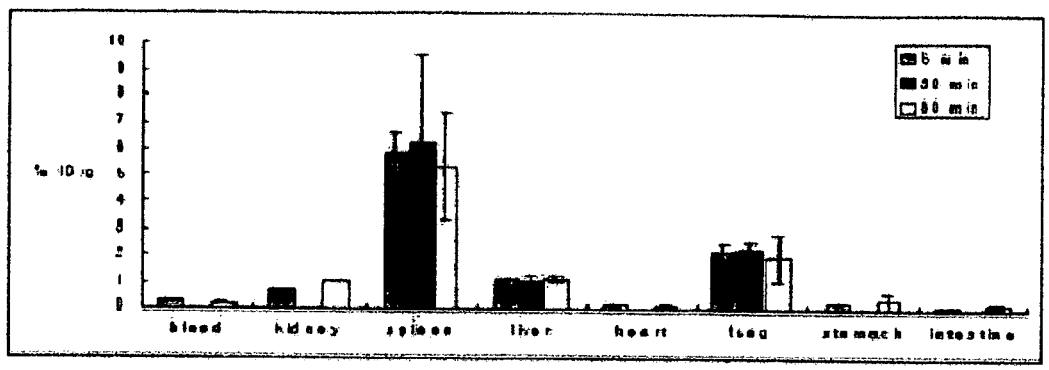
FIGS. 3A and 3B are graphs depicting activities of the $^{99m}$Tc-labeled bis-carboxyethylgermanium sesquioxide ($^{99m}$Tc—Ge-132) nanocolloids injected in organs, expressed as % injected dose/total tissue and % injected dose/g tissue, respectively.
Figure 3B:
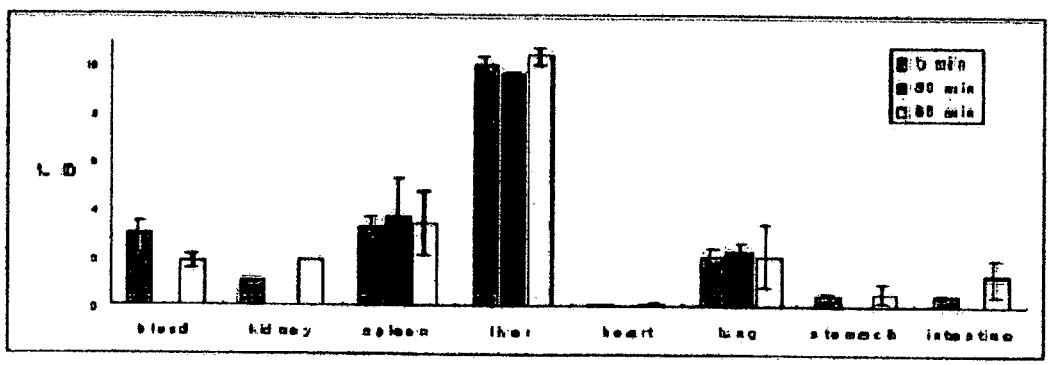

Referring to FIG. 3B, biodistribution data showed that the $^{99m}$Tc—Ge-132 nanocolloids of the invention were accumulated in the reticuloendothelial system (RES) such as spleen, liver and lungs within a half hour after the injection. Especially, as depicted in FIG. 3A, it was observed that the colloids were accumulated relatively high in the spleen. Accordingly, it was found that the $^{99m}$Tc—Ge-132 nanocolloids of the invention could be used as a spleen-imaging agent.

EXPERIMENTAL EXAMPLE 6

Dynamic Data Acquisition and Analysis of $^{99m}$Tc—Ge-132 Nanocolloids

To confirm dynamic kinetics of $^{99m}$Tc—Ge-132 nanocolloids administrated in the body, the following experiment was executed.

Six week-old New Zealand white male rabbits (2887.6±101.5 g, n=3) were anesthetized with ketamine and xylazine and, then, 100 µCi/0.1 ml of $^{99m}$Tc—Ge-132 nanocolloids were injected via the left ear vein of the rabbits. All rabbits were placed in a posterior position. To confirm the dynamic kinetics of the $^{99m}$Tc—Ge-132 nanocolloids, whole body dynamic images for 30 minutes and 16 static images were taken at predetermined intervals using a gamma camera fitted with a low energy all-purpose collimator. Here, a 20% window was centered around 140 KeV. Image data were analyzed under dynamic procedure of a Microdelta system (Siemens, USA). The static images were taken 1.52, 3.45, 5.37, 7.30, 9.22, 11.15, 13.07, 15.00, 16.52, 18.45, 20.37, 22.30, 24.22, 26.15, 28.07, and 30 minutes after the administration using a Microdot imager (Siemens, USA) and the results were shown in FIGS. 4A and 4B.

Figure 4A:
FIGS. 4A and 4B show a gamma image taken at 30 minutes and image scans for 30 minutes after intravenous administration of the $^{99m}$Tc-labeled bis-carboxyethylgermanium sesquioxide ($^{99m}$Tc—Ge-132) nanocolloids into reticuloendothelial system of a rabbit.
Figure 4B:
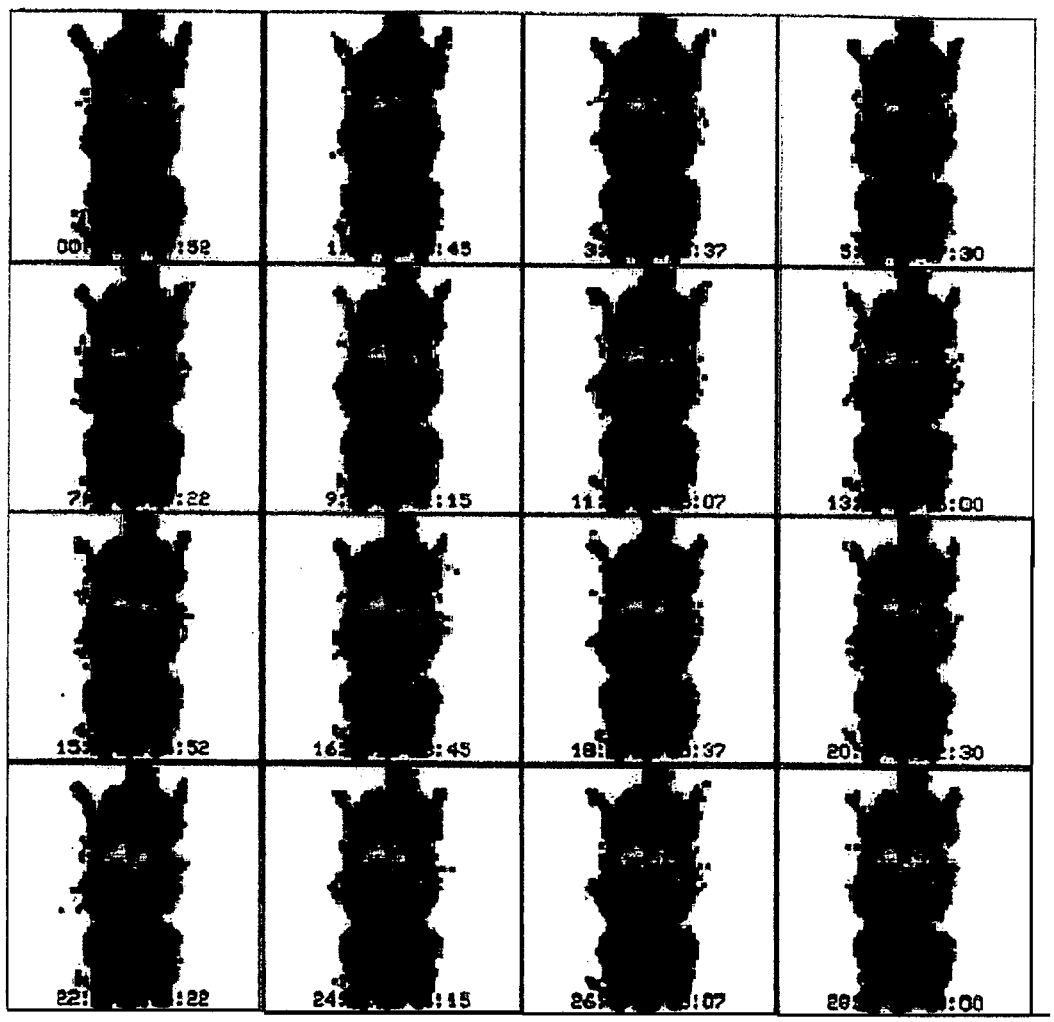

With reference to FIGS. 4A and 4B, it was readily found that the concentrations of the $^{99m}$Tc—Ge-132 nanocolloids were remarkably high in the spleen and the liver. Furthermore, in comparison with images taken via a conventional spleen-imaging agent, the highest accumulation of the $^{99m}$Tc—Ge-132 nanocolloids was observed in the spleen and the rest of the sampled organs were relatively low in amount.

According to the present invention, it is possible to provide $^{99m}$Tc-labeled organic germanium nanocolloids having high labeling efficiency and stability. Moreover, since the $^{99m}$Tc-labeled organic germanium nanocolloids in accordance with the present invention are accumulated in the spleen considerably higher than the conventional spleen-imaging agent, it is possible to use the $^{99m}$Tc-labeled organic germanium nanocolloids of the present invention as a therapeutic radiopharmaceutical for the spleen imaging.

What is claimed is:

1. A method of preparing a $^{99m}$Tc-labeled organic germanium nanocolloid, comprising the steps of:
   (i) preparing an organic germanium colloidal solution by dispersing an organic germanium compound in an aqueous solvent;
   (ii) preparing a solution containing sodium pertechnetate and stannous chloride by dissolving sodium pertechnetate and stannous chloride in an acidic solvent; and
   (iii) adding the solution containing sodium pertechnetate and stannous chloride drop wise to the organic germanium colloidal solution to form a $^{99m}$Tc-labeled organic germanium nanocolloid, wherein the $^{99m}$Tc-labeled organic germanium nanocolloid has Chemcial Formula 1:

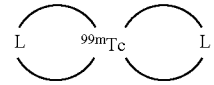

wherein L is selected from the group consisting of bis-carboxyethylgermanium sesquioxide, spirogermanium and lactate-citrate-germanate.

2. The method of claim 1, wherein L is bis-carboxyethylgermanium sesquioxide having Chemical Formula 2.

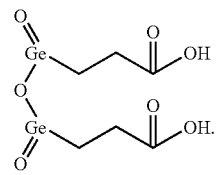

3. The method of claim 1, wherein a pH of the organic germanium colloidal solution ranges from 3.5 to 4.5.

4. The method of claim 1, wherein the acidic solvent is selected from the group consisting of hydrochloric acid, sulphuric acid and nitric acid.

5. A salt form of $^{99m}$Tc-bis-carboxyethylgermanium sesquioxide nanocolloid of Chemical Formula 3:

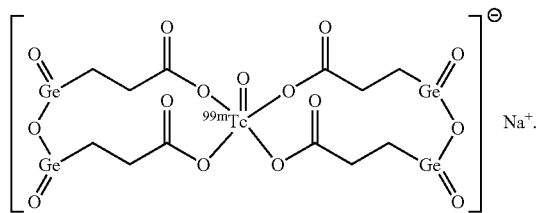

6. A spleen-imaging agent comprising a $^{99m}$Tc-labeled organic germanium nanocolloid of Chemical Formula 1:

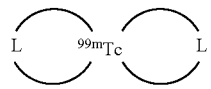

wherein L is selected from the group consisting of bis-carboxyethylgermanium sesquioxide, spirogermanium and lactate-citrate-germanate.

7. The spleen-imaging agent of claim 6, wherein the $^{99m}$Tc -labeled organic germanium colloid is a pharmaceutically acceptable salt form of $^{99m}$Tc-bis-carboxyethylgermanium sesquioxide nanocolloid having Chemical Formula 3:

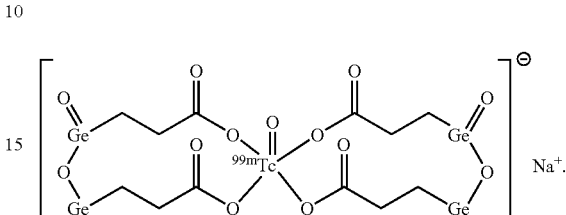

* * * * *